United States Patent [19]

Giannone

[11] Patent Number: 5,691,488
[45] Date of Patent: Nov. 25, 1997

[54] PORTABLE SAMPLING APPARATUS AND SYSTEM

[75] Inventor: Frank S. Giannone, North Bellmore, N.Y.

[73] Assignee: MMC International Corp., Inwood, N.Y.

[21] Appl. No.: 658,316

[22] Filed: Jun. 5, 1996

[51] Int. Cl.$^6$ .................................................. G01N 1/12
[52] U.S. Cl. ............................... 073/863.86; 73/863.82; 73/864.31; 33/717
[58] Field of Search ........................ 73/863.86, 864.63, 73/864.31, 864.24, 864.25, 863.82, 863.85; 33/717, 718

[56] References Cited

U.S. PATENT DOCUMENTS

| | | | |
|---|---|---|---|
| 1,819,058 | 8/1931 | Arnold . | |
| 2,127,296 | 8/1938 | Holmes | 73/863.86 X |
| 2,779,045 | 1/1957 | Harvey | 15/256.51 |
| 4,131,426 | 12/1978 | Range | 141/1 |
| 4,282,624 | 8/1981 | Cobb | 15/220.4 |
| 4,628,749 | 12/1986 | Rafter | 73/863.71 |
| 4,986,138 | 1/1991 | Spencer | 73/864.34 |
| 5,268,150 | 12/1993 | Burkitt | 422/102 |
| 5,408,889 | 4/1995 | Farault | 73/863.71 |
| 5,408,890 | 4/1995 | Klaus | 73/863.81 |
| 5,452,620 | 9/1995 | Giannone | 73/864.31 |

FOREIGN PATENT DOCUMENTS

11525   7/1992   WIPO ...................... 73/863.86

Primary Examiner—Thomas P. Noland
Attorney, Agent, or Firm—McAulay Fisher, Nissen Goldberg & Kiel, LLP.

[57] ABSTRACT

A portable sampling system and method for use with a cargo tank's vapor control valve or other suitable tank entry device to enable an operator to extract and bottle a product sample in place without transfer of the collected sample to another container thereby using the same container for both collection and bottling and without transfer of the collected sample through an open atmosphere. A built-in sampling valve and sample bottle fill attachment are associated with a hand held gauging apparatus for collection of the product sample free of human contact therewith, a vapor return hose assembly couples the built-in sampling valve and bottle fill attachment to the gauging apparatus for eliminating vapor release to the atmosphere and to protect an end user from possible exposure to toxic vapors. A tape reel mechanism is connected with a sampling barrel through which a product sampling tube connected with a tape reel housed in a tape reel housing is lowered into the tank to obtain the product sample, a vapor control valve is coupled between the sampling barrel and the tank, and when the vapor control valve and the sampling valve are opened, the product sampling tube is lowered into the tank through the sampling valve and the vapor control valve, then the product sampling tube is withdrawn and the vapor control valve is closed thereby fluidly disconnecting the reel housing from the tank and any internal pressure, the sampling valve is then closed and the fluid from the product sampling tube is discharged through the sample bottle fill attachment to the container.

17 Claims, 6 Drawing Sheets

PORTABLE SAMPLING APPARATUS AND SYSTEM

BACKGROUND OF THE INVENTION

1. Field of the Invention

This invention is concerned with a closed portable sampling apparatus, and a sampling system and method for obtaining a sample of a liquid product which may be hazardous. More particularly, the invention is concerned with gauging and sampling of liquid bulk petroleum and chemical products.

2. Description of Prior Art

Heretofore, there exists a restricted hand sampling system for measuring the contents of a liquid container system, and this invention is considered to be an improvement over the restricted hand gauging system to provide for ease of use as well as safety.

The "restricted" gauging units are of a design that they are open to the atmosphere, therefore allowing such vapor to escape, and require hand dumping of a collected sample.

U.S. Pat. No. 5,408,889 to Parault is concerned with a sampling device and method for sampling hazardous fluids which comprises a portable device including a housing, containing a ball valve and a device for obtaining fluid from a tank and discharging it into the housing, then pressurizing the housing to discharge the fluid into a sample container, and a by-pass hose solely to return excess fluid to the tank.

Another example of removal of a sample from a tank is disclosed in U.S. Pat. No. 5,408,890 to Klaus. This patent shows a valve through which a sample container is lowered and retrieved with the contained sample. The sample is then forced into a sample container through a complex system using a vacuum pump or nitrogen to push the fluid, and a needle valve assembly to avoid having fumes escape to the atmosphere.

Arnold U.S. Pat. No. 1,819,058 is concerned with taking of samples of liquids from tanks maintained under super-atmospheric pressure.

Spencer U.S. Pat. No. 4,986,138 is concerned with obtaining samples of hazardous nature from fluid flow or process line. This disclosure proposes the use of a vented needle to vent or remove gasses from a sample bottle to a vented line.

U.S. Pat. No. 4,628,749 is concerned with drawing a liquid sample from a process pipeline and transferring the sample into an open container. A complex pair of three-way valves are used for this purpose.

An object of this invention is to provide a closed portable sampling system for sampling bulk petroleum and chemical products, more accurately safer, and without releasing or exposing the operator to toxic or potentially toxic product vapors.

A feature of the closed sampling system is to allow an operator to extract such sample, in safe, efficient, and environmental clean manner not available in a restricted system.

A further object of the invention is to prevent operator exposure to product vapors.

Another feature of the invention is that the traditional physical/actual handling of collected products normally associated with a restricted system is reduced and, for all practical purposes, eliminated at the point of collection. Moreover, operator exposure to any existing or produced vapor is reduced, or substantially eliminated.

A further feature of the invention is the provision of an anti-rotation arm for the tape reel.

SUMMARY OF THE INVENTION

The closed portable sampling system which forms the subject matter of this application is an improvement over prior art restricted systems.

To achieve the above, the system according to the invention provides for individual improvements as well as a unique combination of a vapor return hose assembly, a built-in sampling valve, and a sample bottle fill attachment.

One of the features of the present invention is the use of an integrated sampling diverter valve which operates in conjunction with but independently of a cargo tank's existing vapor control valve. An important feature of this invention is that once the apparatus of the invention is attached to the tank or a storage container, by means of an entry valve or adapter fitting, an operator can use the apparatus forming part of the system and perform the method of the invention both to extract and to bottle a product sample in place without transfer of the collected sample to another container, thereby using the same container for collection and bottling and avoiding any slight possible emission to the atmosphere.

An advantage over the prior art hand gauging systems according to the invention is the use of a unique combination of the vapor return hose assembly, together with the built-in sampling valve and the sample bottle fill attachment which does not require human intervention.

In its broadest aspects, the present invention is concerned with the vapor return hose assembly and a vapor return hose connection, a sampling barrel with the built-in sampling valve and a flow control valve forming part of the bottle fill attachment which upon opening, any interior positive pressure assists in pushing the extracted sample into the sample bottle.

The closed sampling apparatus according to the teachings of this invention includes the vapor return hose assembly, the vapor return hose connection connected to the sampling tape's wiper assembly and comprises a vapor return check valve and the vapor return hose (forming part of the vapor return hose assembly) which has one end coupled to the vapor return check valve connection and the other end coupled with the sampling container or bottle.

The system of the present invention includes an integrated sampling diverter valve which operates in conjunction with but independently of a product tank's existing entry valve. The apparatus which can be attached to any entry valve associated with the product tank is used in conjunction with a sampling valve which forms the subject matter of U.S. Pat. No. 5,452,620 granted on Sep. 20, 1995 in the name of the inventor of the subject matter of this application and assigned to the assignee of this application. An operator can then extract and bottle a product sample in place without the necessity of transferring the collected sample to another container.

To accomplish the objects and features of the invention, the apparatus includes a number of different unique elements to form a closed sampling system. In addition to the aforesaid sampling valve, vapor return hose assembly, sample bottle fill attachment, the apparatus used in the system also includes ancillary equipment comprising tape gauging view ports, a tape reel winding mechanism, an anti-friction tape arm for the tape reel, a sampling barrel and a pressure vacuum balancing button which cooperate with each other to form the elements necessary for carrying out the unique sampling system. The sampling valve which forms part of the aforesaid apparatus can be built into the apparatus as a unit.

The closed unit according to the invention eliminates vapor release, and thereby also protects the end user from possible exposure to potentially toxic vapors.

To these ends, the present invention consists in the provision of a portable sampling system for use with a cargo tank's existing vapor control valve to enable an operator to extract and collect a product sample and bottle the product sample in place without transfer of the collected product sample to another container thereby using the same container for both collection and bottling and without transfer of the collected product sample through an open atmosphere, and comprises a hand held gauging apparatus including a gauging tape, a built-in sampling valve and sample bottle fill attachment for collection of a product sample free of human contact with the product sample, and a vapor return hose assembly for coupling the built-in sampling valve and bottle fill attachment directly back to the hand held gauging apparatus housing for eliminating vapor release to the atmosphere, provide pressure balance within the system, and to protect an end user from possible exposure to toxic vapors.

The invention is also concerned with a closed sampling system, having a product sample retrieval mechanism including a product sampling tube and a vapor return hose associated with the sample retrieval mechanism, a vapor return hose connection connected to a tape wiper assembly which in turn is coupled with the retrieval mechanism through a vapor return check valve and a collected product container associated with the sample retrieval mechanism for receiving the collected product.

A further feature of the invention is the provision of a method for filling a sample container with a collected product while avoiding vapor emission during the collection procedure in which a tape reel mechanism is connected with a sampling barrel through which a product sampling tube is connected with a tape reel and is lowered into a liquid cargo from which a product sample is to be derived, a vapor control valve is coupled with the sampling barrel and a self-contained sampling valve is coupled between the sampling barrel and the cargo container comprising the steps of opening the existing vapor control valve or adapter fitting, and the self-contained sampling valve, lowering the product sampling tube by unfeeling the sample tape coupled with the tape reel through the sampling valve into the cargo container through the vapor control valve, withdrawing the then filled product sampling tube and closing the cargo container's vapor valve thereby isolating the sampling apparatus from the product tank and any internal tank vapor pressure, and closing the built-in sampling valve and discharging the fluid from the product sampling tube, by means of simple gravity flow aided by a normally existing positive cargo tank pressure.

In order that the invention will be more readily understood and carried into effect, the same will now be described in connection with the accompanying drawings.

DETAILED DESCRIPTION OF THE PREFERRED EMBODIMENTS

Figures 1, 1A, 1B:
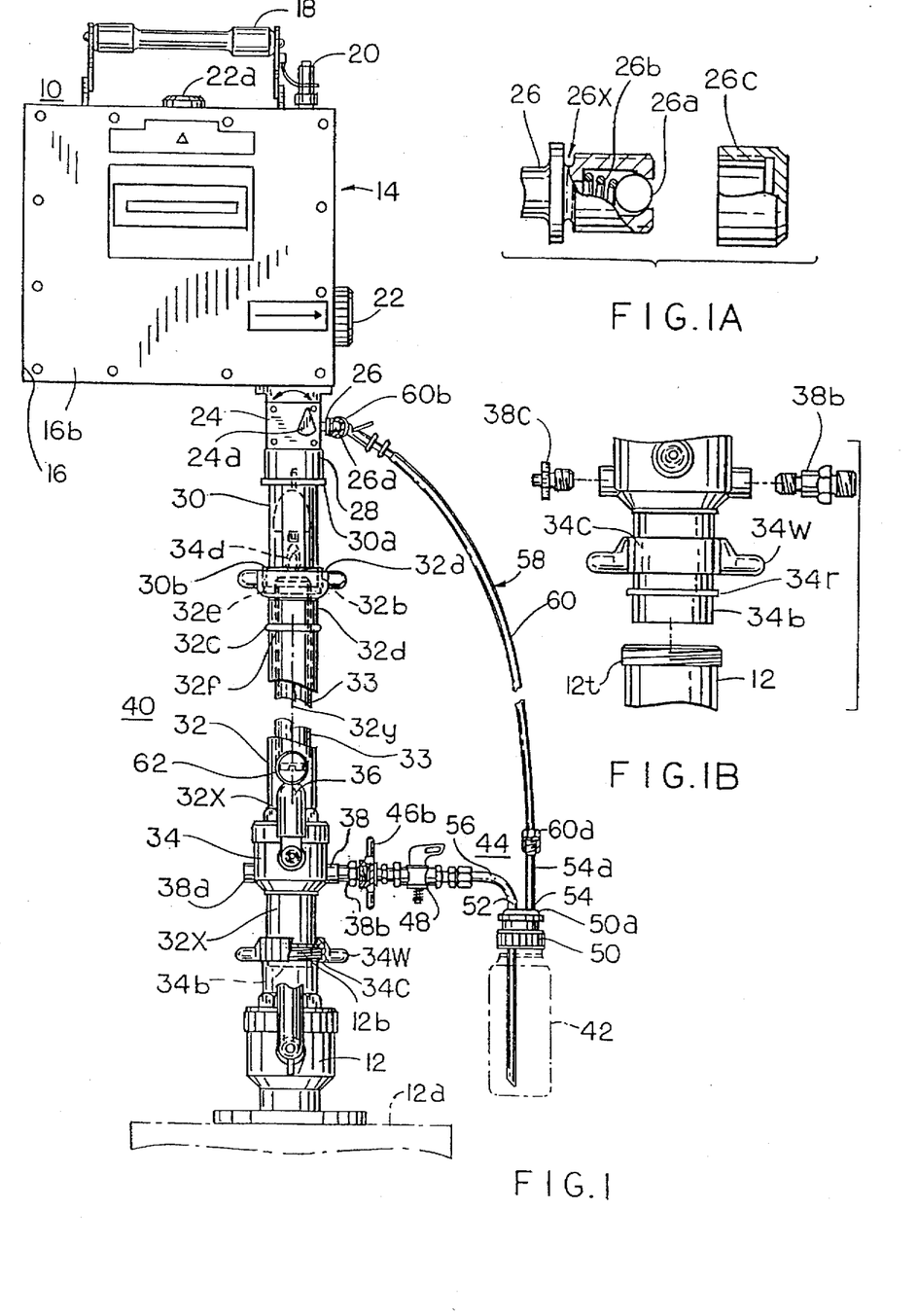
FIG. 1 is a schematic front view of an apparatus for use in connection with the self-contained sampling system according to the invention with the sampling barrel shown in one particular orientation thereof and having a window to view the bottom of a product sampling tube contained within the sampling barrel and of the sampling valve.
FIG. 1A is a detail of an internal spring loaded vapor return check valve.
FIG. 1B is a detail of FIG. 1 showing a connection to a cargo container vapor valve or other pipe-like adapter.
Figure 7:
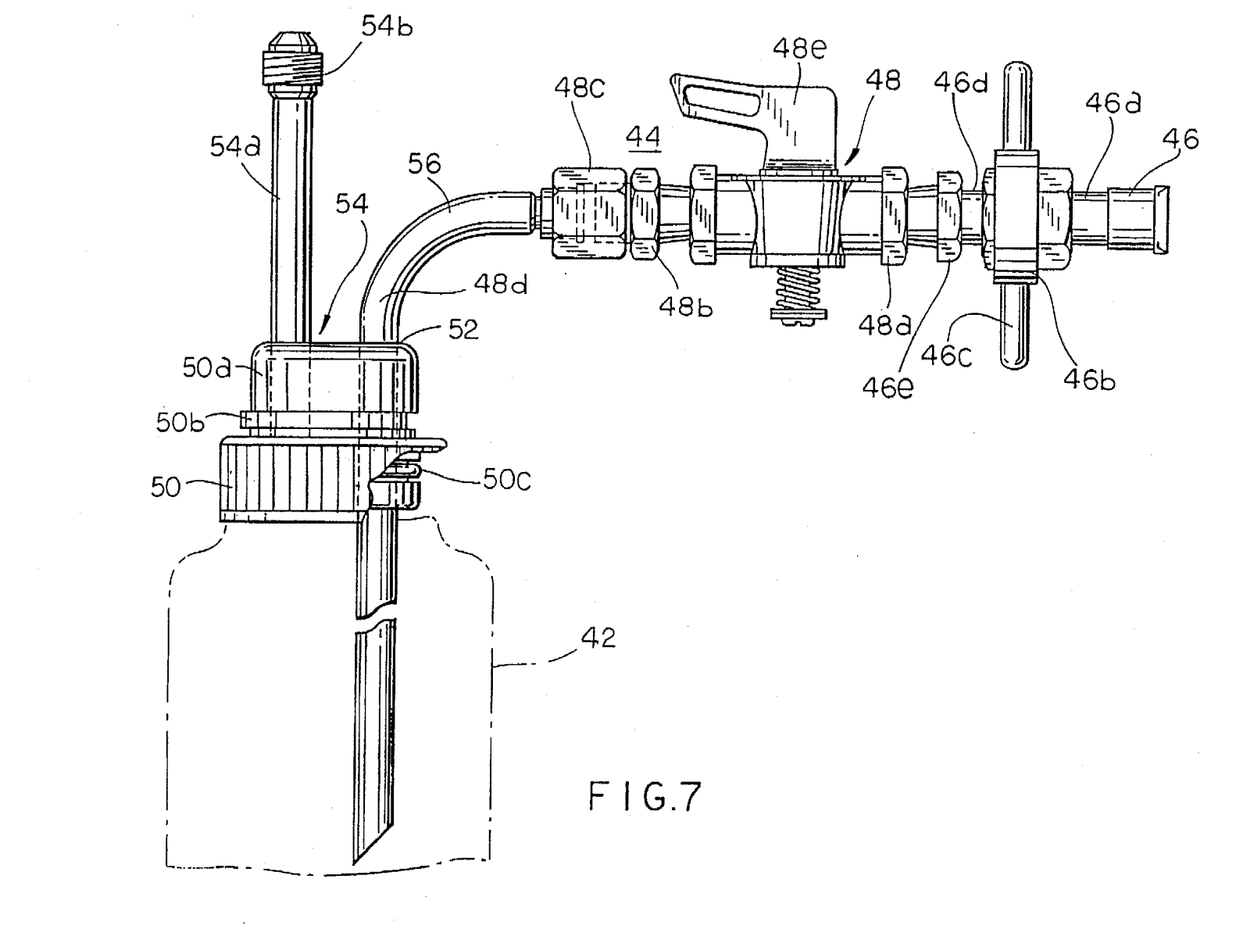
FIG. 7 is a detail of the sample fill and flow control apparatus which is attached between a sample valve drain port connector and a fill bottle or container for sample collection, and upon removal, capped for later laboratory analysis.

Referring now to the drawings, and more particularly to FIG. 1, which shows apparatus 10 for use in direct connection with a conventional existing standard vapor control valve 12 or other equivalent or tank appendage valve, which can be connected to apparatus 10 by means of a suitable adapter, and thereby attached to a cargo or tank container 12a, schematically shown, containing a liquid from which a sample is to be withdrawn and transferred to sample bottle or container 42 through bottle fill attachment assembly 44 (the entire assembly being shown in FIG. 7).

Figure 4:
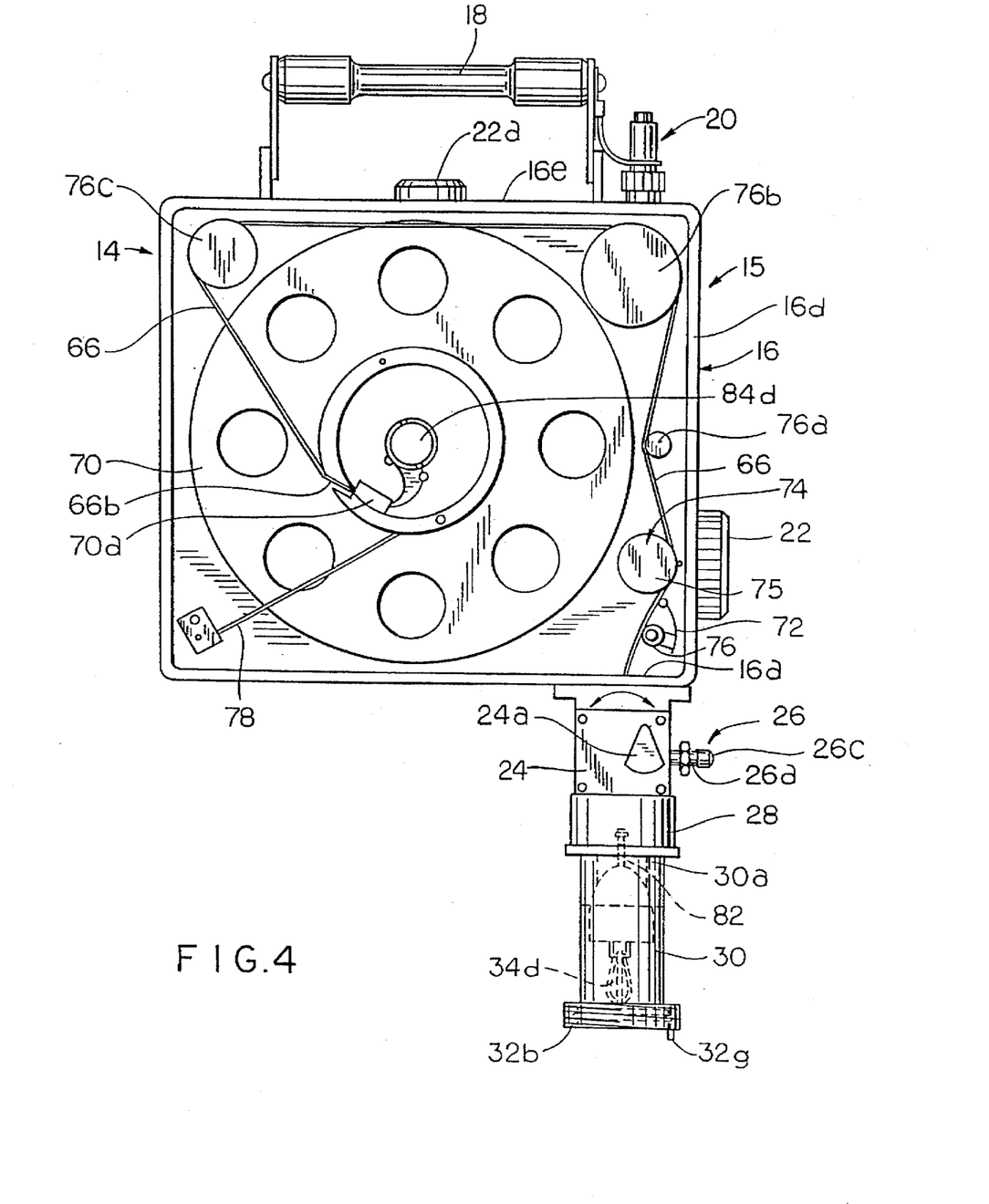
FIG. 4 is an open view of the interior of the casing of the apparatus with the cover removed to show the internal parts and portions thereof coupling the tape reel casing or housing to the sampling barrel.

Apparatus 10 includes a completely enclosed tape and reel mechanism 14 in a casing or reel housing 16 with its exterior cover in place for housing sampling tape and reel mechanism 15 with its exterior cover removed (see FIG. 4). Casing or reel housing 16 is provided with a swing away carrying handle 18 and is pivotally connected to casing or housing 16 for hand carrying the apparatus. A pressure/vacuum valve push button 20 is connected with the top of casing 16 for easy access thereto and for purposes as explained hereinafter. Housing 16 includes at least one sight or view port 22, forming a primary view port, which is preferably provided on the side of the casing 16 and desirably a second view port 22a, forming a secondary view port for tape motion direction is provided under handle 18.

An anti-static treated gauging tape 66, see FIG. 4 is contained and enclosed in casing or housing 16, and the viewing ports 22 and 22a provide the operator with an immediate sense as to whether the unit including tape 66 (FIG. 4) and attached product sampling tube 33 is being raised or lowered. While a single viewing port 22 will be satisfactory for this purpose, it is much easier for the operator to ascertain whether the tape and product sampling tube unit is being moved when two viewing ports are used. Also the operator, may at times, lose a sense of tape direction movement since motion of the tape reel is not directly in view. A fully re-wind tape reading label is posted just below each sight or viewing port indicating the correct tape reading at the fully rewound position. The fully rewound stop position is mechanically set by an internal tape-head stop-bushing 82 (see FIG. 4) located within fie barrel piece attached to the tape wiper housing. It is also recommended that the operator visually sight or view the gauge tape reading to confirm full re-wind condition, before closing the associated vapor control valve or sampling valve 34. This condition can be visually determined by sighting the bottom of product sampling tube 33 through viewing port 62 located at the lower end of sampling barrel tubular assembly 32, prior to releasing the collected product sample.

Tape and reel mechanism 14 includes a member forming a tape wiper housing cover and wiper component mounting plate 24 for housing a tape wiper assembly, and tape wiper actuating knob 24a projecting from and attached to the bottom 16b of casing 16. Member 24 is directly coupled with the base or bottom 16b and also provides for a vapor return check valve fitting 26 to member 24, for connection to a vapor return hose with quick connection end, as later described, herein.

The primary view port 22, located on the side of the reel housing 16, just above member 24 extending from reel housing 16, can be used for tape payout determination without reference to an established gauging platform reference point. When used as such, and due to the equipment construction, a gauging platform reference may be applied to the tape reading for zero level reference correction. Tape wiper actuation knob 24a is provided on member 24.

As will be subsequently explained, a dual purpose winding crank or crank handle 84 (see FIG. 5) is provided. At the completion of a tape payout or rewind operation, the winding crank can be repositioned to serve as a tape reel lock.

In a closed reel housing, an anti-rotation arm 78 (see FIG. 4) is extremely necessary because it would be possible without such anti-rotation arm to bottom out tape payout and then by continued reel turning, cause the tape to be rewound in the opposite direction causing false gauging tape readings, and possible tape fold damage, resulting in short gauging tape life.

Sample bottle or container 42 is connected with vapor return fitting 26 by means of a vapor return and control hose assembly 58 which includes a vapor return hose 60 having one end provided with connector 60a in the form of a thread nut connected to bottle or container 42 and its other end provided with quick connector 60b, for gasket sealed connection to vapor return check valve fitting 26, which houses a spring loaded vapor return check valve 26x including ball 26a and spring 26b. Fitting 26 is externally threaded to receive a quick connector and vapor return check valve depressor 60b for depressing ball 26a and spring 26b, or cap 26c as shown in FIGS. 1A and 4. Quick connector 60b contains a pin depressor for pushing back the sealing ball 26a of spring loaded vapor return check valve 26x, thereby allowing returning vapor communication with the interior of casing 16.

Figure 6:
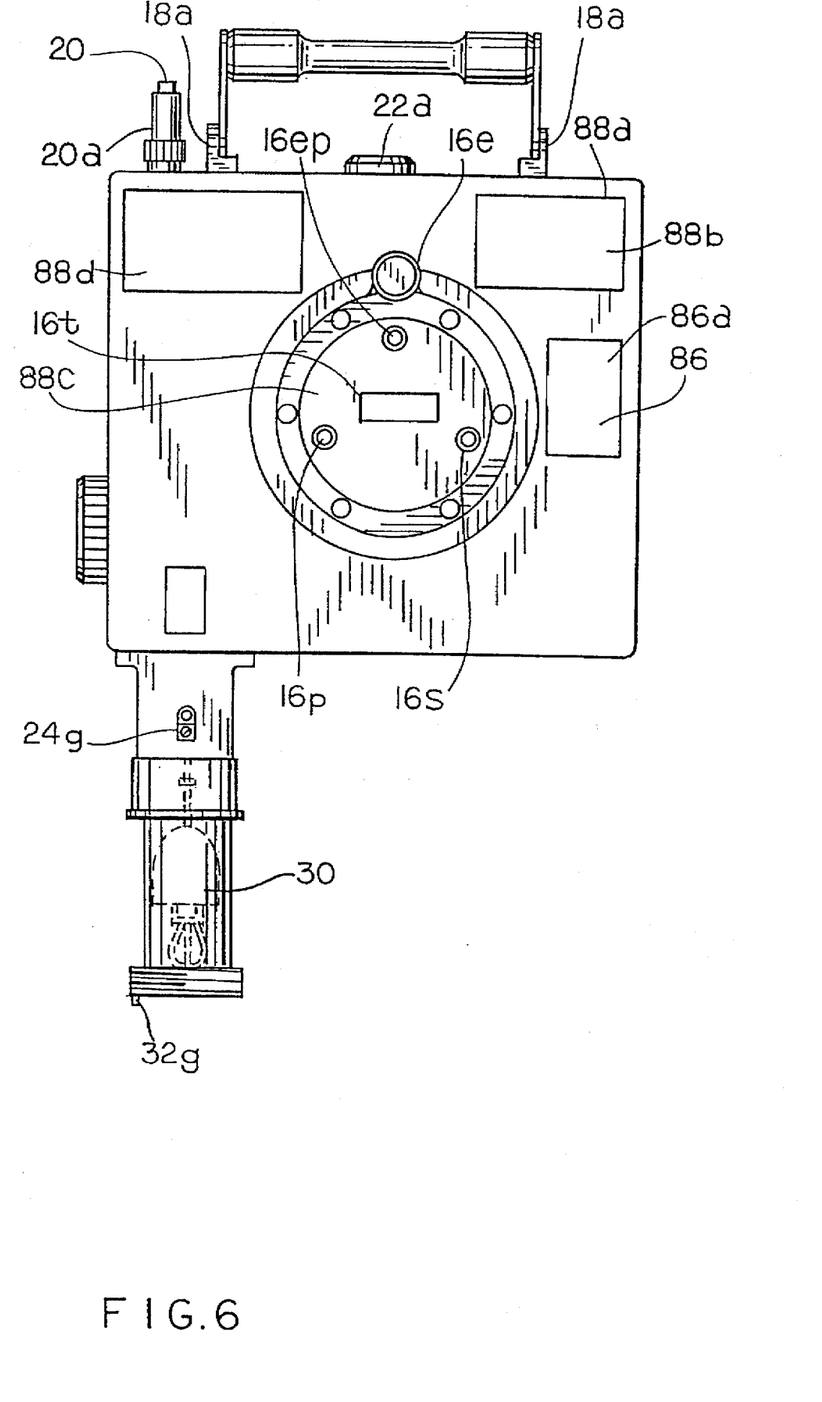
FIG. 6 is another view of the closed gauging unit shown in FIG. 5, showing a rear side thereof opposite to the side shown in FIG. 1, and showing the tape reel winding handle, which also serves as a tape reel positive lock mechanism.

As a safety precaution, the apparatus is provided with a conventional grounding cable and lug 24g, see FIG. 6 which should be connected to a known good hull and vessel ground. The grounding lug 24g provided on the tape wiper housing grounds the entire apparatus 10. A connector 28 at the bottom of member 24 including the tape wiper housing is provided for connection to a stub barrel connector 30 for coupling thereto of an outer tubular member forming sampling barrel tubular assembly 32 for enclosing product sampling tube 33. Stub barrel wiper housing connector 30 has one end 30a connected and sealed with connector 28 connected to member 24 and its other end, having an externally threaded lower stub barrel end 30b connected with sampling barrel 32 by means of upper coupler nut 32a. Sampling valve 34 includes an internal valve member through which internal product sampling tube 33 passes.

Product sampling tube 33 has its upper end connected with a free end of the gauging tape 66 (FIG. 4) and its lower end and passes through sampling valve 34 to enter the cargo or tank container 12a. Valve 34 is connected with built-in sampling valve handle 36 for opening and closing the internal valve member thereof and is shown in its open position with built-in sampling valve handle 36 in its vertical position indicating that the internal member of valve 34 is open. In the open condition of valve 34, handle 36 is axially aligned with the longitudinal axis 32y of the hollow inner tube portion of sampling barrel 32 through which product sampling tube 33 is raised and lowered. Valve 34 also performs the function of a vapor control valve at its position proximate to cargo container 12a. The details of the novel sampling valve are shown as a separate unit in U.S. Pat. No. 5,452,620.

Sampling valve 34 includes at least one outlet drain port 38, which is intended as a primary drain port, for connection to a sample container or bottle 42 (see FIG. 2) by means of a fill attachment assembly 44.

Referring now more particularly to FIG. 7 which shows in detail a connector 46 forming part of fill attachment assembly 44 provided for coupling and uncoupling fill attachment assembly 44 to and from primary drain port 38. Connector 46 includes sleeve tube connector 46a and a pair of wing extensions 46c on eared coupling unit 46b to facilitate rotation thereof for coupling and uncoupling fill attachment assembly 44 to and from outlet drain port 38 by means of sleeve tube connector 46a.

Outlet port 38a (see FIG. 1) is another port which is substantially similar to drain port 38 and is shown with a drain port cover such as cap closure or pipe plug 38c (see FIG. 1B). Outlet drain port 38a is an alternate or optional drain port. Outlet ports 38 and 38a are suitably threaded for primary connection of connector adapter or drain port fitting 38b with inner threaded portion of sleeve tube connector 46a. Port 38a diametrically opposite to and preferably aligned with drain port 38 is a clean out D port, and is provided to facilitate cleaning of sampling valve 34. Drain port fittings 38 and 38a of the sampling valve may each be covered with a threaded seal cap 38c which can be removed before attaching the sampling bottle fill attachment outlet pipe assembly 44 to port 38 or alternate port 38a, which may be used for the same purpose as port 38.

Figure 2:
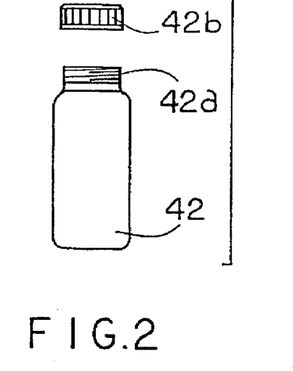
FIG. 2 is a separate view of a sample container or bottle shown in FIG. 1 together with a cap sealing closure for closure of the sample container or bottle.

Sample flow control valve 48 is provided from product sampling tube 33 to control the flow of liquid from sampling barrel 32, after being released, into sample bottle 42 as shown in detail in FIG. 7, collected sample release is later explained. Sample bottle 42 as shown in FIG. 2 is provided with an outer threaded portion or threaded opening end 42a, for mating and sealing engagement with sampling bottle closure cap 42b having inner sealing threads 42c which mate with outer threads 42a. Threads 42a together with an elastomeric seal 42d provide a tight sealing engagement for sealing the contents tightly after a sample has been collected and placed into sample bottle 42.

Sampling bottle 42, when used with apparatus 10 and fill assembly 44, is provided with a separate cap closure such as a seal plug or securing cap 50 which cooperates with fill assembly 44 to transfer a sample from product sampling tube 33 to sample bottle 42, and has an entrance way 52 for use to supply a sample and an exit way 54 for the return of product vapor to the interior of apparatus 10 by means of vapor return hose 60 of vapor return hose assembly 58. Flow control valve 48 has an outlet pipe 56 connected with entrance way 52, and exit way 54 is connected to vapor return check valve fitting 26 through vapor return hose assembly 58 which includes vapor control hose 60 having connector 60a for connection to exit way 54 through connector extension 54a for vapor return tube by means of fitting 54b, then extending therefrom and quick connector 60b for connection to vapor return check valve fitting 26.

The bottle fill attachment may be connected to the sampling valve 34, before or after connecting the sample system to a vapor control valve. As a safety precaution, before connecting the sampling system to the vapor return check valve 26, insure that the flow control valve 48 is in its full closed position.

At the end of the sampling barrel 32 coupled to sampling valve 34, sampling barrel 32 is provided with a window forming part of viewing port 62 for viewing the interior of sampling barrel 32 at its indicated location, and as shown in FIG. 1, the bottom of movable built-in product sampling tube 33 is viewed, also see FIGS. 3A to 3E. Viewing port 62 permits viewing of the product sampling tube 33 and dumped product sample.

Referring to FIG. 1A, at a lower end of the sampling valve 34, a male tubular guide portion 34b is provided for easy entry into the female top threaded portion 12b of an existing vapor control externally threaded vapor control valve 12 or similar tank entry device, lower connector coupler 34c in the form of a nut or collar has a pair of extending turning wings 34w and is provided to couple and decouple coupling potions 12b and 34c to and from each other, respectively. Connector 34 is also provided with an internally threaded portion threaded complementary to outer threaded portion 12t to facilitate rapid connection and disconnection. Tubular guide portion 34b is provided with a stop ring 34r to control the depth of guide portion 34b as it moves into the interior of the standard vapor control valve 12.

Figure 3A:
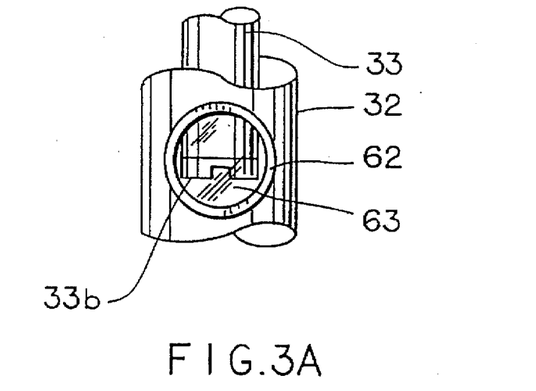
FIG. 3A is a partially detailed enlarged view of the sampling barrel and the bottom of the product sampling tube shown in its full stow or retracted position.
Figure 3B:
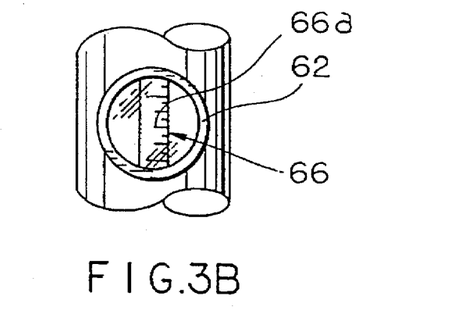
FIG. 3B is a view similar to that of FIG. 3A showing the partially detailed enlarged view of the sampling barrel and a gauging tape contained within the sampling barrel and attached to the product sampling tube with the gauging tape payout and a display of the payout distance to product surface level at the window port above the sampler valve at approximately six inches above the top of the vapor control valve as shown in FIG. 1.
Figures 3C, 3D, 3E:
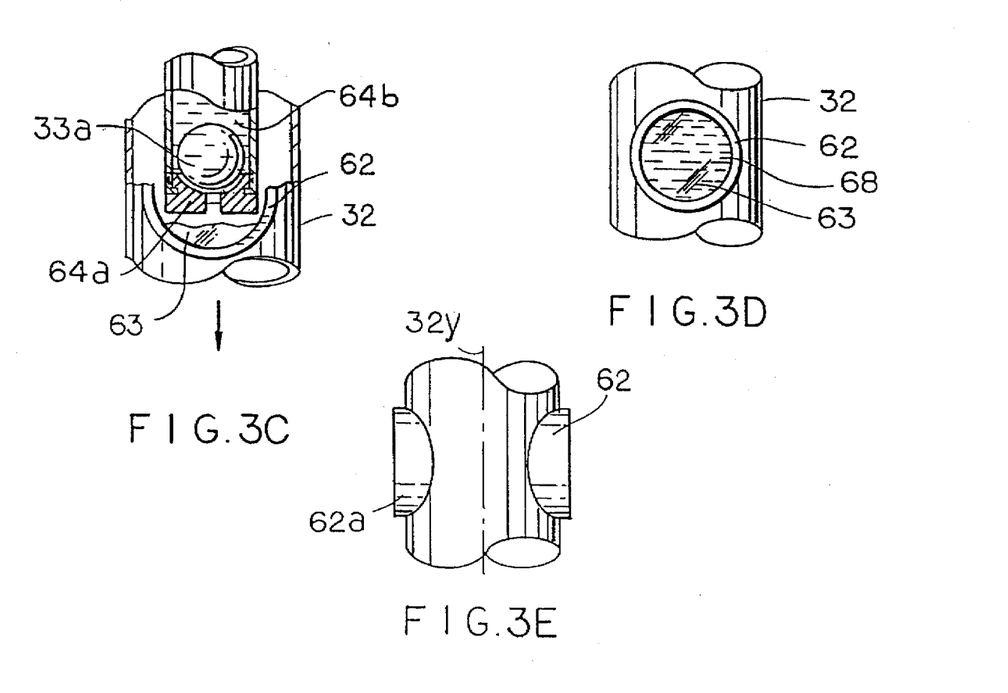
FIG. 3C is a view generally similar to that of FIG. 3A, but with the product sampling tube raised for viewing through the window and showing the product sampling tube having a portion cut away illustrating the product sampling tube ball check valve containing a sample with the tape raised to its full stow mark in the tape reel.
FIG. 3D is another view of the sampling barrel having a product sampling tube contained therein, but lowered to a position below the window and not visible with a sample of the liquid sample contained within the product sampling tube which was previously discharged upon leaving the product sampling tube after obtaining the sample and now the sample is contained in the area/volume within the sampling barrel for subsequent discharge through the sampling valve, via a sample bottle fill attachment (see FIG. 7) into a sample bottle (see FIGS. 1 and 2).
FIG. 3E is a modification of the sampling barrel shown in FIGS. 3A to 3D with an additional window.

Referring now more particularly to FIGS. 3A to 3E, and in particular to FIGS. 3A and 3C which show the bottom of product sampling tube 33 having a lower end portion which is a ball check valve assembly 64, and a portion of the sampling barrel 32. Sampling barrel 32 near the lower end thereof is provided with at least one viewing port 62 and preferably a second viewing port 62a, preferably diametrically opposite to viewing port 62 for axial alignment therewith.

In FIG. 3A, product sampling tube 33 is shown in a first position thereof, and in FIG. 3B, the product sampling tube 33 has been further lowered into cargo container 12a so that gauging tape 66 is visible through window or viewing port 62 or 62a. The FIG. 3A position is also a fully rewound condition. Product sampling tube 33 in FIG. 3A is shown in its full stow position with the unit or apparatus 10 attached to vapor control valve 12 which is opened for entry of product sampling tube 33 into cargo container 12a. The sampling valve 34 and vapor control valve 12 are both open so that product sampling tube 33 can be lowered to the desired ullage level in tie cargo container. FIGS. 1 and 3A show product sampling tube 33 with the tape fully rewound.

FIG. 3A, indicates tie commencement of operation, and the bottom 33b of the product sampling tube 33 is seen as it would appear with its associated gauging tape at its fully rewound and locked condition.

The position of the product sampling tube 33 as viewed through sight port 62 is preferably six inches above the top of the vapor control valve 12.

In the FIG. 3B position, the tape is shown in an unwound condition thereof in its condition with the bottom or base 33b or the bottom of product sampling tube 33 in the cargo container 12a after it has been lowered for collection of a sample of the fluid contained in the cargo container.

FIG. 3C shows the product sampling tube 33 or bottom 33b after a sample has been collected and withdrawn, and the product sampling tube 33 has a portion partially cut away at 64b, to show a check valve ball 33a and a liquid sample 68 contained therein. The filled product sampling tube 33, is shown returned to its full stow position. Gauging tape reel 70 should at this time be locked in place by means of reel drum handle lock 84b, and handle 84 is shown moved to its vertical position. The built-in sampling valve is then rotated to its closed position. FIG. 3D shows the liquid sample 68 as viewed through window 62 after the release thereof from the product sampling tube 33 into the barrel 32 of sampling valve 34, and prior to discharge through bottle fill assembly 44 into container 42. Here the product is filling the view port window 62, after the product sampling tube 33 which is provided with a ball check valve to hold the sample in the product sampling tube 33 until released by a mechanism to raise the ball and have the sample discharge through sample valve 34, once the sampling tube has been lowered, and the internal check valve ball 67 of product sampling tube 33 is raised as described in U.S. Pat. No. 5,452,620. The sampling valve is a positive shut-off ball, valve, and handle 36 is rotatable through an angle of 90° to open and to close the ball valve.

After product sampling tube 33 has been slowly lowered into the cargo container to the desired ullage level, product sampling tube 33 is steadily raised to the full stow position of the tape in housing 16 to its full stow mark and the tape is locked to prevent any furrier movement thereof, and to the position shown in FIG. 3C. Sampling valve 34 is then closed sealing off any pressure from container 12a pressure.

FIG. 3E shows a partial view of tubular assembly sampling barrel 32 with window or primary viewing port 62 on one side, and a similar viewing window or secondary viewing port 62a at about 180° displaced or diagonally opposite thereto to provide two in-line view ports. While it is possible to use a single view port, as noted heretofore, it is preferred that two windows or sample barrel view ports diagonally opposite to each other, 62 and 62a be provided to provide better lighting for viewing of the gauging tape 66, and to provide an in-line view port arrangement.

The gauging tape viewing ports 62 and 62a are preferably covered with specially tempered glass elements covers 63. These tempered glass covers 63 are easily removed for cleaning or replacement purposes.

At times due to ambient temperature conditions, and interior product tank temperature differences, condensation may appear on the main housing view ports, but this does not interfere with this operation.

View ports 62, 62a on sampling barrel 32 are preferably situated approximately six (6) inches above the sampling barrel end connected to sampling valve 34. The center of the sampling barrel view ports 62, 62a are in line with the zero ullage preference plane.

This built-in sampling valve 34 is a sub-assembly which connects the sampling barrel 32 to a fixed vapor control valve and is the connector 34c which includes lower coupling nut or collar for connection to any fixed vapor control valve, such as a "B" series MMC made available by the assignee of this application.

Short stub barrel connector 30, attached to connector 28 containing the reel housing wiper assembly at stub barrel wiper housing connector end 30a, remains in place when the sampling barrel tubular assembly 32 is removed for storage and the product sampling tube 33 is detached from the gauging tape 66.

Threaded joint 32b at the upper end of the sampling barrel tubular assembly 32 and stub barrel piece 30 are "O" ring sealed by means of O-ring 32c when threaded and joined together.

The location of thread joint of internally threaded coupling ting 32b has been chosen to allow easy snap hook assembly d the product sampling tube 33 to the gauging tape by means of hook 34d, see FIGS. 1 and 4.

Figures 5, 5A:
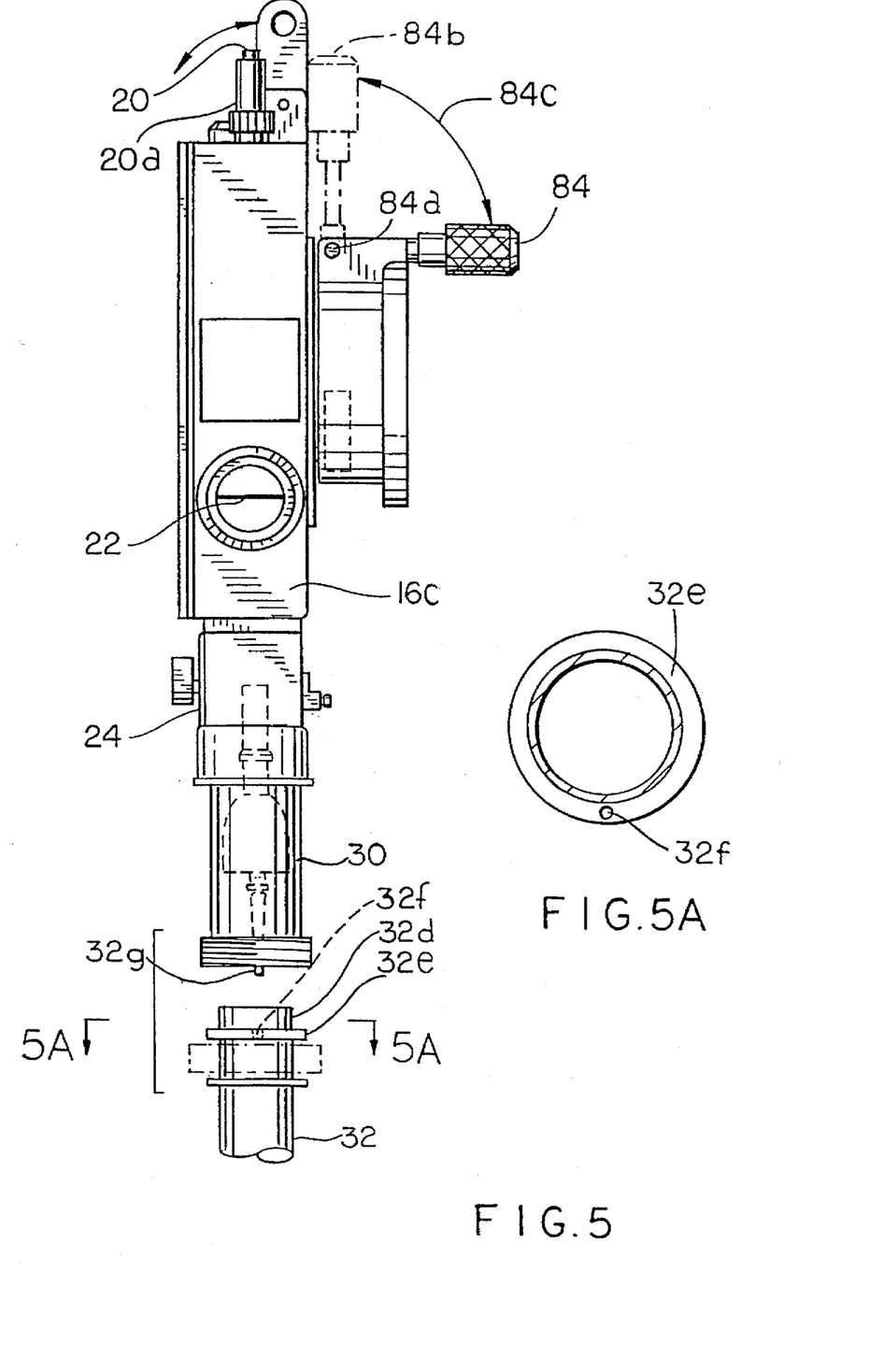
FIG. 5 is a schematic side view of the closed sampling unit showing a full view of an additional gauging tape viewing port on its narrow case side and also showing a section of a portion or partial modification of the sampling barrel.
FIG. 5A is a sectional view of the sampling barrel tubular assembly taken on line 5A—5A of FIG. 5 showing an alignment ring and pin alignment hole.

Referring now more particularly to FIGS. 5 and 5A, top end 32d of sampling barrel tubular assembly 32 has a fixed ring 32e with pin alignment hole 32f (see FIG. 5A) drilled in it, which is adapted to receive a locator pin 32g extending from the externally threaded stub barrel connector 30 for alignment of stub barrel connector 30. Fixed ring 32e prevents upper coupler nut 32a from sliding down barrel tubular assembly 32. FIG. 6 also shows locator pin 32g extending from stub barrel connector 30.

When sampling barrel tubular assembly 32 has been seated within stub barrel connector 30, internally threaded coupling ring 32b, attached to the sampling barrel 32, is threaded to the stub barrel piece 30. The attachment is completed with the graduated tape face marking, properly aligned in the viewing port for reading purposes.

With gauging tape 66 substantially fully re-wound, (see FIG. 3C) the bottom or base 33b of the product sampling tube may be seen through the sampling barrel view port 62. Sampling barrel view port 62 or 62a also becomes another means d determining a substantially fully stowed tape.

Referring now more particularly to FIG. 4 which shows tape and reel mechanism 14 including housing 16 with one side of casing or housing 16 removed to show interior portions and sampling tape and reel mechanism 15.

The interior of housing 16 contains an inlet 16a to housing 16 schematically shown for tape 66. Positioned within housing 16 is reel 70 having a molded epoxy tape end piece 70a, for the gauging tape and ground wire attachment, to which one end 66b of tape 66 is held. Tape 66 which enters housing 16 though inlet 16a passes over splash guard 72 and then passes over tape guide and cursor pin assembly 74, which includes cursor pin 75 schematically shown as a roller, and then around guide rollers 76 including idler roller 76a, tape guide rollers 76b grid 76c for connection with the reel 70 by means of the tape end piece 70a. Anti-rotation spring-loaded arm 78 is coupled with reel 70 to prevent on unwonted payout of tape 66 and reel 70 god to stop reel motion when the tape 66 is fully extended.

When the apparatus is used for sampling purposes, primary viewing port 22 on vertical side 16d (as conventionally hand held and as shown in the drawings) and second view port 22a located at the top 16e of the tape reel housing are normally used for viewing the approximate payout of the gauging tape 66 and its product sampling tube 33. These view ports ore preferably physically located one foot or its metric equivalent apart from each other, as the tape moves along the tape path. Since the gauging tape for U.S. purposes contains feet designations, the viewing ports ore separated one foot apart. Of course, separation based on metric dimensions are all useable to satisfy the conditions as used outside of the U.S. If the container is to be made solely for metric purpose usage and a tape with metric designation on it is used, then a metric spacing can also be used.

The secondary viewing port 22a also serves another important function which is to provide the operator with on immediate sense as to whether the tape and attached product sampling tube 33 is being raised or lowered. This is particularly important for a closed system. This is not a trivial requirement, because the gauging tape 66 is effectively in a closed box or environment and the operator may at times lose the particular or actual sense of tape direction movement as the reel is in motion. The direction or tape movement measurement, other than through the windows, is not directly in view. Also, the operator can readily determine if the rewind has been completed.

As a very important second purpose, by viewing the tape reading at either the primary or secondary port when an operator thinks that a gauging tape has been fully re-wound, the operator can immediately determine whether or not the tape has been fully and completely re-wound. A full re-wind tape reading level and stop position is posted just below each sight port indicating the correct tape reading at the fully re-wound position. The fully re-wound stop position is mechanically set by an internal tape head stop bushing 82, located within stub barrel connector 30 which is attached to the tape wiper housing 24 by means of connector 28 to the stub barrel wiper housing connector end 30a.

During operation, the operator should visually sight the gauged tape reading to confirm a full re-wind before closing the vapor control valve 12 and the sampling valve 34.

The primary view port 22 located on the side of tape reel housing 16 just above the tape wiper assembly 24 can be used for tape payout determination without reference to an established zero reference point. When used as such, and in response to equipment construction, a zero ullage correction must be applied to the sighted tape reading to assure an accurate reading.

The bottom of reel housing 16 is provided with conventional drainage (not shown) to allow any product accumulation due to excess product dripping from a re-wound tape, to return back and through member 24 (tape wiper assembly) and sampling barrel 32, to cargo tank 12a.

Reel housing cover 16b, see FIGS. 1 and 5, should be removed periodically for interior inspection and clean-out, as necessary. More viscous products will require greater cleaning. The interior of the main sampler system is nylon coated throughout, and other interior parts are either nylon coated or treated to allow easy clean-out with any standard cleaning solution.

Referring now more particularly to FIGS. 5 and 6, winding crank 84 (see FIG. 5) is provided to wind the tape and unwind the tape. Winding crank 84 is shown in full outline in FIG. 5, and it is pivotable about pivot 84a to its fully stowed position with the handle shown at 84b in dashed outline juxtaposed to the side of housing 16 when not used for winding and in its locked condition. At the completion of either a tape payout or re-wind operation, the winding crank is re-positioned in the vertical direction as shown in dotted outline at 84b and, in this position, it functions as a tape reel lock. Crank handle or winding crank 84 pivots through an arc 84c from a vertical position 84b shown in dashed outline to a horizontal position relative to longitudinal axis 32y. The use of the spring-loaded anti-rotation arm 78 follows the sampling tape payout and will stop reel motion when the tape is fully extended. The anti-rotation arm in the closed reel housing prevents a bottoming out of tape payout and then, continues reel turning to re-wind the tape in the opposite direction. Winding crank 84 is coupled with reel 70 by means of bushing 84d (see FIG. 4, cover 16b is removed).

Member 24 which includes the tape wiper housing is positioned between main reel housing 16 and stub barrel connector 30 contains spring loaded tape wiper actuation knob 24a. When re-winding gauging tape 66 to its full stow position, it is recommended that a tape wiper be used.

Spring loaded anti-rotation arm 78 follows the sampling measuring or gauging tape payout, and will stop reel 70 motion when a tape is fully extended. Anti-rotation arm 78 is a necessary, as well as a desired element in the closed reel tape housing. Because of a lack of direct access to cargo container 12a, it is possible without notice for the tape to bottom out and then, by continued reel turning, to cause the tape to re-wind in the opposite direction.

Figure 2A:
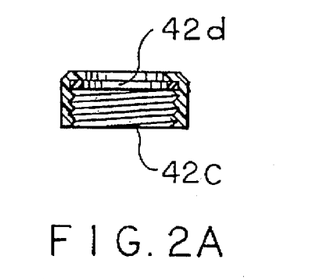
FIG. 2A is a sectional view of the cap sealing closure for the sample container of FIG. 2.

Sample bottle 42 as shown in FIG. 2 includes outer threads 42a to receive cap closure 42b, see FIG. 2A, provided with inner sealing threads 42c. After a sample has been placed into bottle 42, cap closure 42b, is placed onto the mouth of the sample bottle 42 and inner sealing threads 42c mate with outer sealing threads 42a, and cap closure 42b is pressure tightened against sealing O-ring comprising elastomeric seal 42d and is locked into place onto bottle 42. Hand tightening of the cap closure 42b is all that is necessary. Vapor escape from the connected bottle is prevented by the elastomeric sealing O-ring 42d.

Referring now more particularly to FIG. 7 which shows bottle fill attachment assembly 44 with connector 46 connected to container 42 from outlet drain port 38 and fill tube connector 48d from cap 50 to sample flow control valve 48. Cap 50 includes entrance way 52 for receiving outlet tube or connector 48d. Connector 46 is connected to drain port 38 (see FIG. 1) for feeding a sample to bottle 42 through assembly 44. Coupling fill assembly 44 to sampling valve drain port 38 is accomplished by threading on connector 46 by means of eared coupling nut 46c to the drain port fitting 38b of sampling valve 34. Normal hand tightening of this connection is sufficient for leak tight operation.

Bottle fill cap closure 50 includes a seal plug bottle holder 50a coupled to retaining ring 50b. Cap closure 50 is partially cut away to show internal O-ring 50c, to prevent vapor escape, on an internal threaded part of the cap to provide aright seal with complementary outer threads 42a (see FIG. 1 ) on the outer rim of bottle 42.

Entrance way 52 is an opening for receiving fill tube connector 48d through seal plug 50a and exit way 54 is coupled with vapor return tube 54a and male connection fitting end 54b for connection with vapor return hose assembly 58, see FIG. 1.

Fill tube connector 48d is connected through sample flow control valve 48 to sleeve tube connector 46a for connection to outlet drain port 38. Coupling tube 46d is connected to bushing pipe 46e for connection with sleeve tube 46a. Coupling nut 46c is connected to an inlet side of in-line flow control valve 48 through pipe and bushing locking nut 48a and the outlet side of control valve 48 is coupled through connector tube and locking nut 48b to fill tube connector 48d through coupler/ decoupler 48c for rapid connection and disconnection with pipe or fill tube 48d.

As can also be seen in FIG. 7, in-line flow control valve 48, is similar to sampling valve 34 in that each is of the type of a positive shut-off ball valve, requiring only a turn of handle 48e through 90° to open or to close. Operations are always begun by insuring that all valves are in theft fully closed position.

Vapor return hose 60 is connected at connector end 60a to make connection end 54b of vapor return tube 54a extending out of container 42 through cap 50 to the sample fill attachment, and at the other end by means of connector 60b to vapor return hose quick connection fitting 26. Connector 60b depresses ball 26a, and thereby allows free gas or vapor flow between the fill attachment and the closed interior gauging housing 16.

Connector 60b must be fully and firmly seated to the check valve fitting 26 to ensure opening of the check valve.

Fitting 26 completes the means for completing the displaced collection bottle vapor path back into the closed system, thereby creating a pressure balance between container 42 and housing 16, and provides a completely closed pathway. Balancing of the vapor flow path established by the vapor return hose 60 provides for a safety feature such that an unwanted burst of product sample into the sample bottle does not occur.

Vapor control hose assembly 58 provides an important function of avoiding a negative pressure above the outgoing fluid collected from an atmospheric system so that flow is not diminished to a trickle. The condition is avoided since outgoing fluid will displace an equal volume of air being vented from the sample collection bottle via the vapor return hose, back into the closed system, thus maintaining the pressure balance within the system.

Pressure vacuum valve push button 20 is depressed to assure complete drainage of the extracted sample through push button valve 20a. Button 20 is not depressed during sample collection, but it can be optionally depressed when all of the product sample is thought to have been drained.

After all attachments between assembly 44 and port 38 are completed, unlock the tape and lower the tape for approximately three inches or until a stop can be felt due to a lack of pull on the tape. At this point, the product can be seen discharged from the product sampling tube through window 62 in FIG. 3D and (or the other side, window 62a, not shown), the product is observed as filling the opening.

Open the sample flow control valve 34 by means of handle 36, as seen in FIG. 1, and product drainage can now be viewed through window 62. Then open the sample flow control valve 48 of bottle fill attachment assembly 33 by means of handle 48e to fill sample bottle 42. After a sample is taken, sample flow control valve 48 is then closed. If no further samples are to be taken, sampling valve 34 may be returned to its open to tank position by handle 36, and closing off exit way to attachment assembly 44, at which position the valve sample ports 38 and 38a are sealed off from container 12a. To insure full opening of the ball check valve at the bottom of the sample tube, the sampling valve ball has a built-in spring loaded pusher pin as disclosed in U.S. Pat. No. 5,452,620 which is released when the sampling valve is placed into its closed position. This feature insures free passage product sampling tube 33 through the valve.

The same procedure is also necessary even if one starts with a clean sample bottle 42. Flow control valve 48 is opened to allow a sample to fill bottle 42 and displace clean air in bottle 42; this preliminary procedure is necessary in order to avoid any vapor emission, and to empty sealed container 42, sampling barrel 32, housing 16 and product sampling tube The procedure for filling sample bottle 42 is as follows:

Both vapor control valve 12, and sampling valve 34 and sample flow control valve 48 are opened, then product sampling tube 33 and gauging tape 66 are lowered while allowing some dwell time, as indicated by the position shown in FIG. 3B with gauging tape 66 visible through window viewing port 62. Then product sampling tube 33 is steadily raised to its full stow position (see FIG. 3).

After visually confirming the full stow position at either the primary sight view port 22 or secondary sight port 22a, the tank's vapor control valve 12 is closed, thereby fluidly disconnecting housing 16 from the tank container 12a, and any internal tank pressure. Sampling valve 34 is then closed, and its spring loaded push button (see U.S. Pat. No. 5,452,620) is permitted to rise to engage ball 33a.

Product sampling tube 33 is then lowered and, in doing so, pushes up its internal ball check valve, indicated by ball 33a, allowing a fluid product to flow out of the product sampling tube 33 into the interior of vapor valve barrel 32 and into sampling valve 34 and through bottle fill attachment assembly 44 to bottle 42. Sample flow control valve 48 is then closed.

With vapor return hose 60 connected to the vapor return check valve fitting 26, a pressure balance between the interior housing pressure and sample bottle is established. As the bottle is filing and thereby displacing the air/vapor mixture within it, a declining but balancing pressure is being maintained within the bottle. Therefore, a sudden burst of fluid or liquid into the sample bottle will not occur, and fluid or liquid flow will be mainly due to simple gravity flow as the material flows downwardly.

Normally, with the minimum amount of pressure capacity trapped within the sampling assembly or system, at or near completion of bottle filling, little or no positive pressure remains trapped in the system. Before removing a filled sample bottle, close sampling valve 34 and disconnect the vapor return hose assembly 58 from vapor return hose fitting 26.

The balancing vapor flow path established by the vapor return hose prevents an unwanted burst of product sample into the sample bottle.

Liquid which is now at the bottom of container tank 12a, can be compared to a metal can, with a mixture of air and product vapor above it. When the sample flow control valve 48 is opened, product from tank 12a in product sampling tube 33 will begin to fill bottle 42, and at the same time, vapor return hose assembly 58 returns to the system the same amount of air displaced from the sample bottle 42. If the same amount of air displaced from sample bottle 42 were not returned through, vapor return hose assembly 58, a negative pressure above the outgoing fluid would be developed. If this condition were allowed, product flow would soon diminish to a trickle.

While there has been shown what is considered to be the preferred embodiments of the invention, various changes and modifications may be made without departing from the scope of the invention.

What is claimed is:

1. In a closed sampling system, including a product sample retrieval mechanism and a vapor return hose associated with said product sample retrieval mechanism;
   a vapor return hose connection connected with a tape wiper assembly coupled with said retrieval mechanism through a vapor return check valve;
   a vapor return hose associated with said product sample retrieval mechanism; and
   a sampling container associated with said product sample retrieval mechanism and coupled with said vapor return hose.

2. In the closed sampling system as claimed in claim 1, comprising:
   means including a vapor control valve and a sampling valve adapted for connection with a cargo tank containing a fluid to be sampled; and
   means coupled with said product sample retrieval mechanism for lowering and raising said product sample retrieval mechanism into and out of the cargo tank and passing through said vapor control valve and said sampling valve, said sample retrieval mechanism including a product sampling tube, and means for discharging the sample through said sampling valve into the sampling container.

3. In the system as claimed in claim 2, including a bottle fill attachment assembly adapted to be connected between said sampling container and said sampling valve.

4. In the sampling system as claimed in claim 3, wherein said fill attachment assembly includes a connector for coupling and uncoupling said fill attachment assembly from a drain port associated with said sampling valve through which the sample is discharged into the sampling container.

5. In the sampling system as claimed in claim 2, wherein said means coupled with said product sample retrieval mechanism includes a sample tube lowering means associated with said sampling valve.

6. In the system as claimed in claim 1, including a sampling barrel associated with a sample tube lowering means connected with said sampling valve; said sampling barrel including means for viewing the contents of said sampling barrel.

7. In the system as claimed in claim 1, including a tape reel housing containing a reel and tape mechanism coupled with said tape wiper assembly for passing the tape through said tape wiper assembly for obtaining a sample of a fluid in a closed container, a product sampling tube connected with said tape beyond said tape wiper assembly, at least one viewing port associated with said housing for providing an operator with an immediate sense as to whether the tape is being lowered or raised.

8. In the system as claimed in claim 7, wherein said reel and tape mechanism includes an anti-rotation arm.

9. In the sampling system as claimed in claim 7, including two viewing ports associated with said housing.

10. In the sampling system as claimed in claim 9, including an internal tape-head stop bushing located within a barrel piece attached to said tape reel housing.

11. In the system as claimed in claim 1, including sampling flow control means adapted to be coupled to said sample retrieval mechanism and said sampling container for transferring a sample of fluid obtained by said retrieval mechanism to said sample container, said vapor return hose returning vapors transferred to the sample container through said flow control means from said sample retrieval mechanism.

12. In the system as claimed in claim 11, wherein said sample retrieval mechanism includes a sampling barrel and a product sampling tube movable through said sampling barrel into a container containing a fluid to be sampled, said sampling barrel including at least one view port for viewing the interior of said sampling barrel.

13. In the system of claim 12, including a vapor valve securing collar for said sampling barrel.

14. In the system of claim 1, wherein said sampling container is provided with a cap closure for closing off the contents and a cap closure mechanism having an entrance way and an exit way, said entrance way being coupled with said sample retrieval mechanism, and said exit way being coupled with said tape wiper assembly through said vapor return hose to provide for a balanced vapor flow path so that an unwanted burst of product sample into the sample container does not occur, and further so that a partial vacuum is not created within said enclosure during the draining of a collected product sample.

15. In the sampling system as claimed in claim 1, comprising a hand held gauging apparatus including a built-in sampling valve associated with said product retrieval mechanism for collection of a product sample free of human contact.

16. In the sampling system as claimed in claim 1, wherein said vapor return hose is coupled with a built-in sampling valve adapted for connection with a cargo tank containing a fluid to be sampled.

17. In the sampling system as claimed in claim 1, wherein said vapor return hose connection includes a vapor return check valve fitting housing a spring loaded vapor return check valve.

* * * * *